United States Patent [19]

Kobayashi

[11] Patent Number: 5,600,011

[45] Date of Patent: Feb. 4, 1997

[54] HAFNIUM COMPOUND AND A PROCESS

[75] Inventor: Shu Kobayashi, Tokyo-to, Japan

[73] Assignee: Daicel Chemical Industries, Ltd., Osaka, Japan

[21] Appl. No.: 474,651

[22] Filed: Jun. 7, 1995

[30] Foreign Application Priority Data

Jul. 8, 1994 [JP] Japan .................................. 6-180849

[51] Int. Cl.$^6$ ............................. B01J 27/02; B01J 27/135
[52] U.S. Cl. ........................... 568/335; 502/216; 502/227
[58] Field of Search ................................ 502/216, 227; 568/335

[56] References Cited

PUBLICATIONS

Kobayashi et al., Tetrahedron Lett., (1996), 37(12) pp. 2063–2066.
Crotti et al., Tetrahedron lett., (1996), 37(10), pp. 1675–1678.

*Primary Examiner*—Asok Pal
*Attorney, Agent, or Firm*—Sughrue, Mion, Zinn, Macpeak & Seas

[57] ABSTRACT

Disclosed are a novel hafnium compound represented by the formula $Hf(OSO_2CF_3)_4$ and a process using a hafnium compound represented by the formula $Hf(OSO_2CF_3)_4$ as a catalyst in a Friedel-Crafts reaction.

3 Claims, 3 Drawing Sheets

HAFNIUM COMPOUND AND A PROCESS

FIELD OF THE INVENTION

The present invention relates to a novel hafnium compound represented by the formula $Hf(OSO_2CF_3)_4$.

Furthermore, the present invention relates to a process using a hafnium compound represented by the formula $Hf(OSO_2CF_3)_4$ as a catalyst in a Friedel-Crafts reaction.

BACKGROUND OF THE INVENTION

A Friedel-Crafts reaction has been conventionally used as a nuclear substitution reaction of an aromatic compound.

H. O. House "Modern Synthetic Reactions" 2nd Ed. W. A. Benjamin, California (1972) pp 734–816 discloses that the reaction in which an aromatic compound is allowed to react with halogenated alkyl compounds, olefins, acid halides, acid anhydrides, esters, ethers, and cyclic ethers in the presence of Lewis acid-based catalysts such as anhydrous aluminum chloride, ferric chloride, boron trifluoride, zinc chloride, titanium tetrachloride, stannic chloride, magnesium chloride, gallium chloride, and aluminum bromide, etc., whereby an alkyl group, an acyl group, and an alkoxy group, etc. can be introduced into the aromatic compound.

In a Friedel-Crafts reaction, halogenated hydrocarbons may be generally employed or not as a reaction solvent.

Also, a novel catalyst has been proposed, for example, Japanese Patent Unexamined Publication (Kokai) No. 320089/1993 discloses a process for acylation of an aromatic compound using a Friedel-Crafts reaction in which a rare-earth elements-based Lewis acid represented by formula $RE(OSO_2Rf)_3$ [wherein RE is a rare-earth element, and Rf is a perfluoroalkyl group or perfluoroalkoxy group] is employed as a catalyst.

As catalysts to be employed in a Friedel-Crafts reaction, its diversity has been being pursued without being satisfied with catalysts known in the present time from a viewpoint of activity, treatments after reaction, recovery and regeneration, reaction solvents suitable for the catalysts, scopes of applicable reaction, price, and methods for preparing, etc., and further more preferred new catalysts are being expected in the existing circumstances.

As a result of an intensive investigation by the present inventor, it was found that a specified hafnium compound is novel, and it is useful as a catalyst for a Friedel-Crafts reaction, and the present invention was accomplished.

SUMMARY OF THE INVENTION

It is an object of the present invention to provide a novel hafnium compound. It is another object of the present invention to provide a process using the hafnium compound as a catalyst in Friedel-Crafts reaction.

A first aspect of the present invention relates to a novel hafnium compound represented by the formula $Hf((OSO_2CF_3)_4$.

A second aspect of the present invention relates to a process which comprises using a hafnium compound represented by the formula $Hf(OSO_2CF_3)_4$ as a catalyst in a Friedel-Crafts reaction.

DETAILED DESCRIPTION OF THE INVENTION

Figure 1:
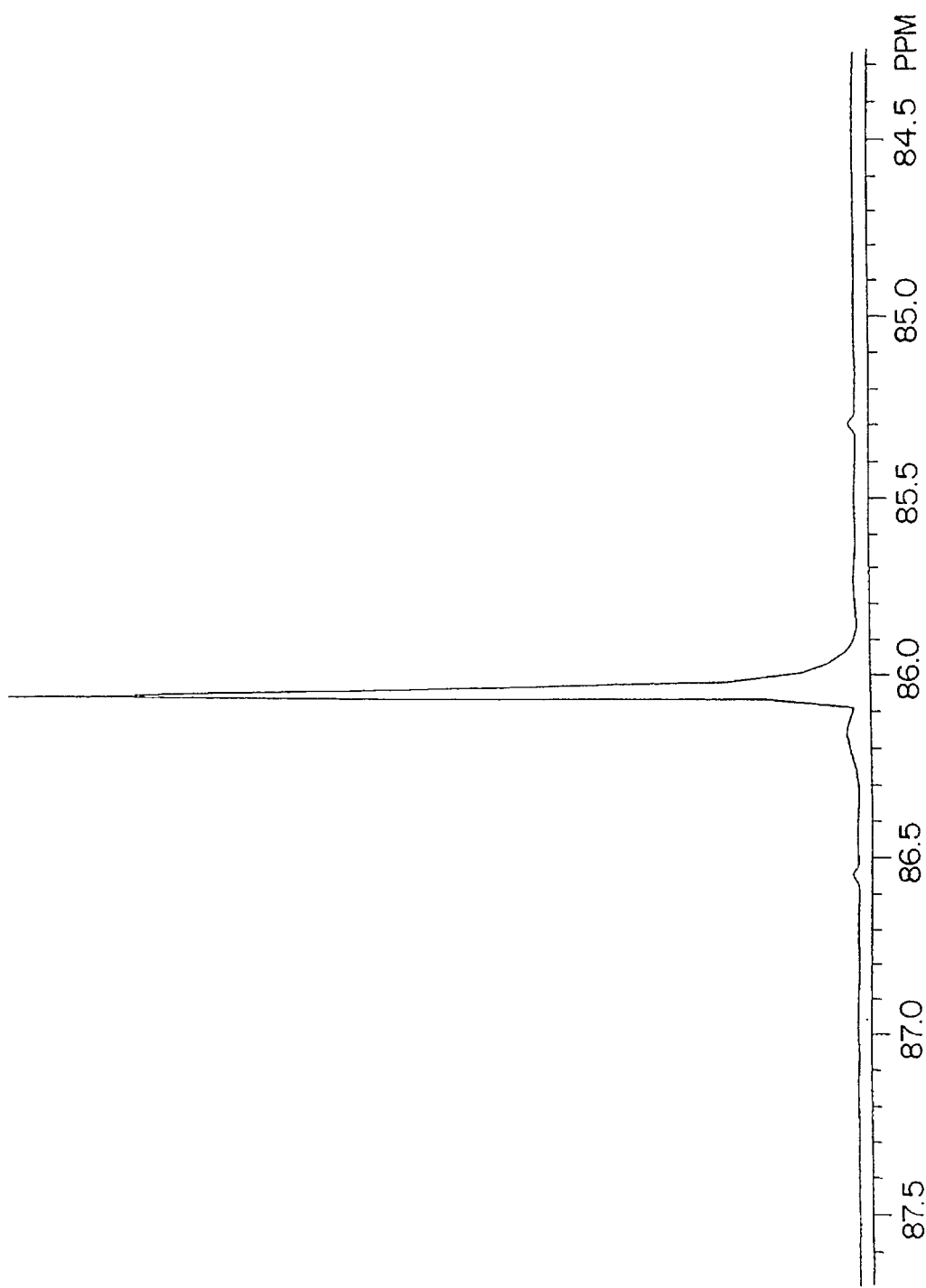
FIG. 1 is a $^{19}$F-NMR chart in relation to the novel hafnium compound of the present invention.

The present invention will be described hereinafter in more detail.

According to a first aspect of the present invention, there is provided a novel hafnium compound represented by the formula $Hf(OSO_2CF_3)_4$.

According to a second aspect of the present invention, there is provided a process which comprises using a hafnium compound represented by the formula $Hf(OSO_2CF_3)_4$ as a catalyst in a Friedel-Crafts reaction.

As a specific example of Friedel-Crafts reactions in which the hafnium compound is preferably employed as a catalyst, there is exemplified an acylation reaction using an acid anhydride.

The hafnium compound represented by the formula $Hf(OSO_2CF_3)_4$ of the present invention is a compound named hafnium trifluoromethane sulfonate, which can be prepared by the reaction of hafnium tetrachloride ($HfCl_4$) with trifluoromethanesulfonic acid($CF^3SO^3H$). The reaction may be carried out in the presence or absence of solvents, more preferably in the absence.

In the absence of solvents, an excessive amount of trifluoromethane sulfonic acid results in playing a role as a solvent.

The molar ratio of hafnium tetrachloride ($HfCl_4$) to trifluoromethane sulfonic acid ($CF^3SO^3H$) ranges from ¼ to ¹⁄₁₀₀, preferably from ¼ to ¹⁄₁₀. The two compounds are usually reacted at a temperature range from 0° to 200° C., preferably from 30° to 100° C. for 1 to 100 hours, preferably 1 to 5 hours in the atmosphere of an inert gas such as argon, helium, and nitrogen. Even in the case of more than 100 hours, there is no problem.

After the completion of the reaction, an excessive amount of trifluoromethane sulfonic acid is removed by evaporation to obtain a hafnium compound of the present invention. If necessary, the hafnium compound obtained can be purified by conventional methods which include washing with a solvent such as petroleum ethers, methylene chloride, acetonitrile, and toluene, etc.

In the case when the above-described reaction is carried out in the presence of solvents, for example, methylene chloride, acetonitrile, and toluene, etc. are employed which are inert in the reaction and can preferably dissolve the starting compounds.

The hafnium compound of the present invention is can be preferably employed as a catalyst in a Friedel-Crafts reaction.

As compounds applicable in a Friedel-Crafts reaction, there are exemplified noncondensed aromatic hydrocarbon compounds such as benzene, etc., aromatic hydrocarbon compounds having condensed ring such as naphthalene, anthracene, etc., and aromatic compounds having condensed heterocyclic ring such as indole, and quinoline, etc.

The aromatic compounds may include substitute groups such as halogens, alkyl groups, alkenyl groups, aryl groups, alkoxy groups, thio groups, and amino groups so far as the reaction is not hindered.

The aromatic compounds are allowed to react with the above-mentioned halogenated alkyl compounds, olefins, acid halides, acid anhydrides, esters, ethers, and cyclic ethers to introduce substituted groups.

The Friedel-Crafts reaction in which the above-mentioned hafnium compound of the present invention can be employed includes an alkylation, acylation, and alkoxylation, preferably acylation.

In the case when the hafnium compound of the present invention is employed as a catalyst in the Friedel-Crafts reaction, there may be employed conventional solvents for a Friedel-Crafts reaction such as nitromethane instead of the above-mentioned halogenated hydrocarbons which have a bad influence on global environments.

Although the present invention is illustrated below by Examples in detail, it is not limited by those.

EXAMPLE 1

A 100-milliliter four-necked flask equipped with a tube for supplying an inert gas, a thermometer, a reflux condenser, and a stirrer was charged with 17.22 g (53.8 millimole) of hafnium chloride having a purity of 99.9% (manufactured by Soegawa Physics & Chemistry, Ltd.), followed by adding 44.2 milliliter (500 millimole) of trifluoromethane sulfonic acid.

The flask was heated at 50° C. for 68 hours in an argon atmosphere, followed by removing an excessive amount of trifluoromethane sulfonic acid by evaporation at a reduced pressure to obtain a crude hafnium trifluoro-methane-sulfonate powder.

The powder was washed four times with 30 milliliter of a petroleum ether to obtain a white-colored powder. The white-colored powder obtained was further dried at 50° C. for 8 hours in a reduced pressure to obtain 41.8 g of a purified hafnium trifluoromethane sulfonate with a yield of 100%.

Properties are as follows.

$^{19}$F-NMR (CD$_3$CN, delta):
86.0 (s) (external standard: hexafluorobenzene, 0.00 ppm); the chart is shown in FIG. 1.

Figure 2:
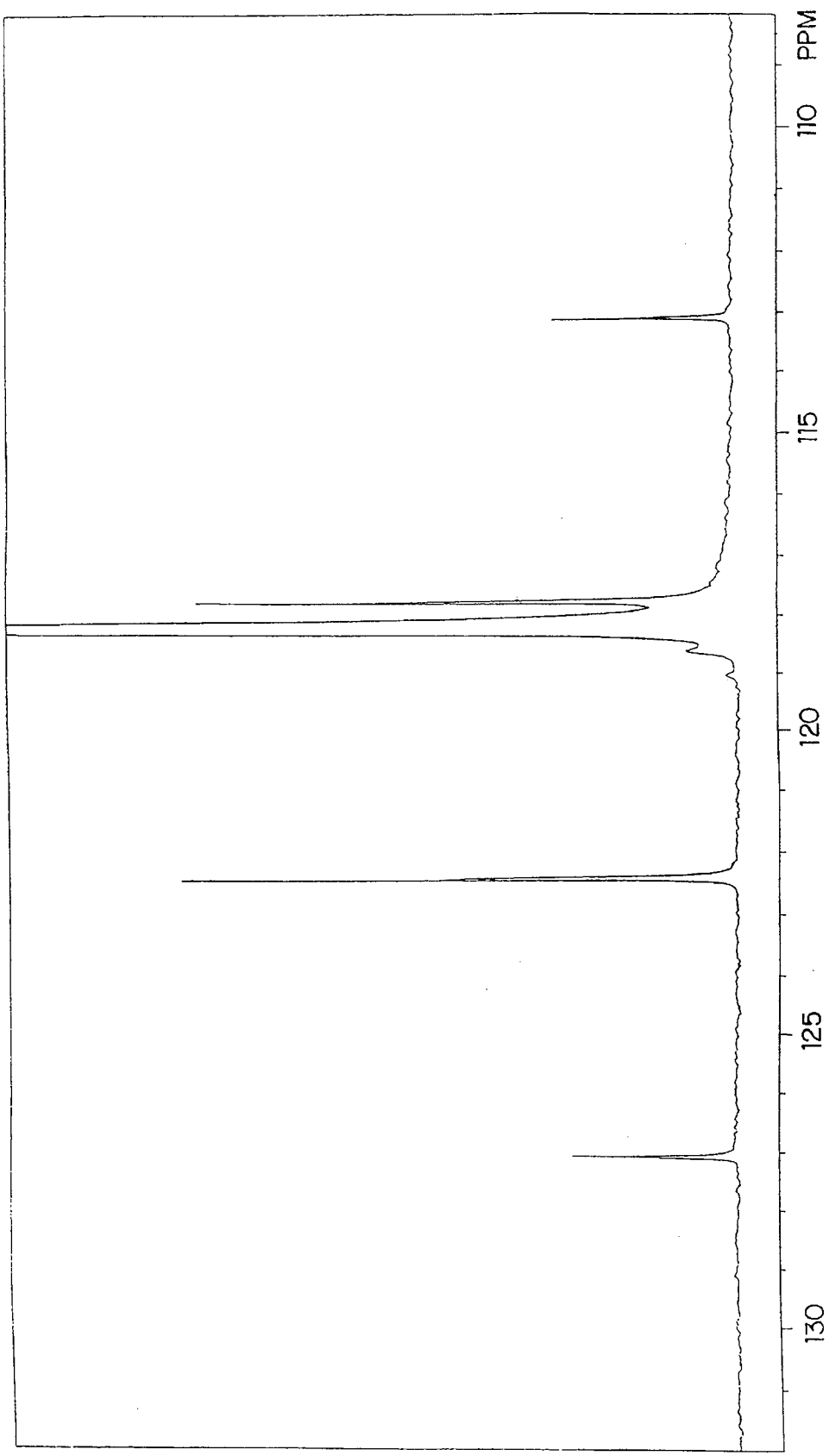
FIG. 2 is a $^{13}$C-NMR chart in relation to the novel hafnium compound of the present invention.

$^{13}$C-NMR (CD$_3$CN, delta):
127.1 (s), 122.4 (s), 117.8 (s), 113.1 (s) (external standard: hexafluorobenzene, 0.00 ppm); the chart is shown in FIG. 2. Elementary analysis (%):
Hf (an emission spectroanalyzer) 22.02 (theoretical value: 23.05),
S (elementary analysis) 16.02 (theoretical value: 16.53), C
(elementary analysis) 6.23 (theoretical value: 6.20), O (elementary analysis) 23.56 (theoretical value: 24.79), F (by ion-chromatography)

Figure 3:
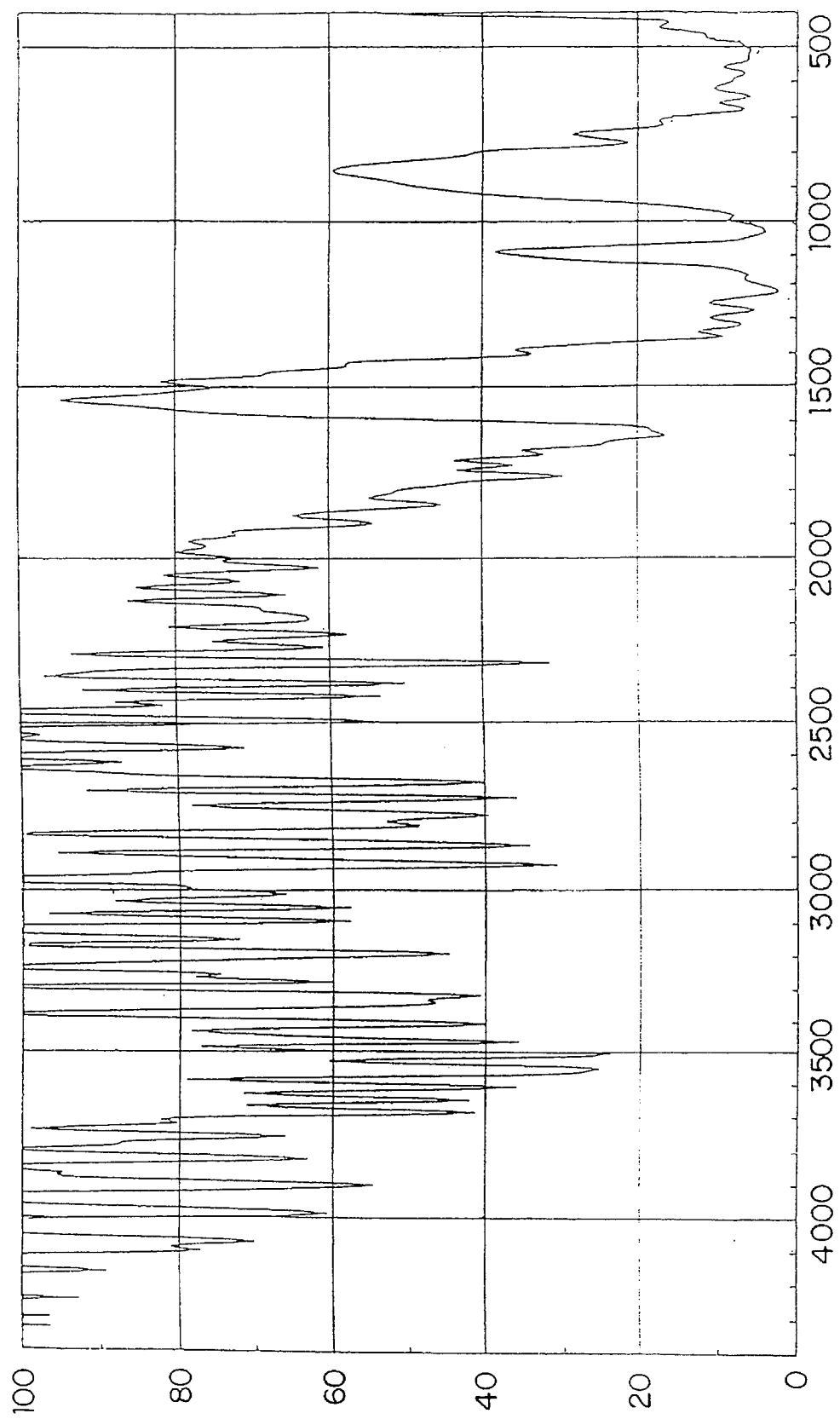
FIG. 3 is an IR chart in relation to the novel hafnium compound of the present invention.

IR (KBR):
1637, 1350, 1311, 1267, 1209, 1161, 1030, 985, 715, 675, 638, 573, 534, 513, 463, 426 cm$^{-1}$; the chart is shown in FIG. 3, in the chart, the ordinate exhibits transmissivity (%), the abscissa exhibits wave number (cm$^{-1}$).

By the above analyses, it was confirmed the hafnium trifluoro-methanesulfonate has the chemical formula of Hf(OSO$_2$CF$_3$)$_4$.

EXAMPLE 2

4 millimole of lithium perchlorate (LiClO$_4$) was mixed with 0.02 millimole (1 mol% based on mesitylene) of Hf(OSO$_2$CF$_3$)$_4$ obtained in Example 1, followed by adding 2 millimole of mesitylene, 4 millimole of acetic anhydride, and 1 milliliter of nitromethane at room temperatures to obtain a mixture. Thus obtained mixture was stirred for 6 hours at the same temperatures, followed by adding a saturated solution of sodium hydrogencarbonate to form an organic layer and water layer.

The organic layer was separated, and the water layer was extracted with dichloromethane. The organic layer and a solution extracted with dichloromethane were mixed each other, followed by dried with anhydrous sodium sulfate. Solvents were removed from the mixture by evaporation at reduced pressures, followed by distilling to obtain 2,4,6-trimethylacetophenone with a yield of 92%.

EXAMPLE 3

The same procedures were followed as in Example 2 except that 0.04 mol% of Hf(OSO$_2$CF$_3$)$_4$, 30 millimole of mesitylene, 4M of LiClO$_4$, and 15 milliliter of CH$_3$NO$_2$ were employed to obtain 2,4,6-trimethyl-acetophenone with a yield of 68%.

EXAMPLES 4–16

The same acylation procedures were followed as in Example 2 except that aromatic compounds shown in Table 1 in place of mesitylene, acid anhydrides shown in Table 1, and 5 mol % (10 mol % in only Example 8) of Hf(OSO$_2$CF$_3$)$_4$ were employed. Products and yields are also shown in Table 1.

EXAMPLE 17

The same procedures were followed as in Example 2 except that lithium perchlorate alone was not employed to obtain 2,4,6-trimethylacetophenone with a yield of 92%.

TABLE 1

|  | Aromatic compound | Acid anhydride | Reaction Product | Yield |
| --- | --- | --- | --- | --- |
| Example 2 | mesitylene | acetic anhydride | A | 92% |
| Example 4 | anisole | acetic anhydride | B | 95% |
| Example 5 | 1,2-dimethoxybenzene | acetic anhydride | C | 90% |
| Example 6 | o-xylene | acetic anhydride | D | 90% |
| Example 7 | m-xylene | acetic anhydride | E | 91% |
| Example 8 | toluene | acetic anhydride | F | 85% |
| Example 9 | naphthalene | acetic anhydride | G | 99% |
| Example 10 | anisole | isopropionic anhydride | H | 100% |
| Example 11 | anisole | t-butyric anhydride | I | 91% |
| Example 12 | anisole | propionic anhydride | J | 93% |
| Example 13 | mesitylene | propionic anhydride | K | 94% |
| Example 14 | m-xylene | propionic anhydride | L | 83% |
| Example 15 | m-xylene | benzoic anhydride | M | 88% |
| Example 16 | mesitylene | benzoic anhydride | N | 94% |

It is to be noted that abbreviations in Reaction Product of the Table 1 are as follows.
A: 2,4,6-trimethylacetophenone
B: 4-methylacetophenone C: 3,4-dimetoxyacetophenone
D: 3,4-dimethylacetophenone
E: 2,4-dimethylacetophenone
F: 4-methylacetophenone
G: acetylnaphthalene
H: isopropyl 4-methoxyphenylketone
I: t-buyl 4-methoxyphenylketone
J: 4-methoxyphenyl propylketone
K: 2,4,6-trimethylphenyl propylketone
L: 2,4-dimethylphenyl propylketone
M: 2,4-dimethylbenzophenone
N: 2,4,6-trimethylbenzophenone Furthermore, it is to be noted that 3 mol % of 2-methylacetophenone is included in Example 8, and that acetylnaphthalene in Example 9 is a mixture of 1-acetylnaphthalene/2-acetylnaphthalene=52/48.

While the invention has been described in detail and with reference to specific embodiments thereof, it will be apparent to one skilled in the art that various changes and modifications can be made therein without departing from the spirit and scope thereof.

What is claimed is:

1. A novel hafnium compound represented by the formula $Hf(OSO_2CF_3)_4$.

2. A process which comprises using a hafnium compound represented by the formula $Hf(OSO_2CF_3)_4$ as a catalyst in a Friedel-Crafts reaction.

3. A process as set forth in claim 2, wherein said Friedel-Crafts reaction is an acylation reaction in which an acid anhydride is employed.

* * * * *